United States Patent
Yanagi et al.

(10) Patent No.: US 11,255,022 B2
(45) Date of Patent: Feb. 22, 2022

(54) HOLE FORMING METHOD, MEASURING APPARATUS AND CHIP SET

(71) Applicant: HITACHI, LTD., Tokyo (JP)

(72) Inventors: Itaru Yanagi, Tokyo (JP); Rena Akahori, Tokyo (JP); Kenichi Takeda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/905,035

(22) Filed: Jun. 18, 2020

(65) Prior Publication Data

US 2020/0332434 A1 Oct. 22, 2020

Related U.S. Application Data

(62) Division of application No. 15/104,325, filed as application No. PCT/JP2013/084551 on Dec. 25, 2013, now Pat. No. 10,724,147.

(51) Int. Cl.
*C25F 3/14* (2006.01)
*G01N 33/487* (2006.01)
*C12Q 1/6869* (2018.01)
*G01N 27/447* (2006.01)

(52) U.S. Cl.
CPC .............. *C25F 3/14* (2013.01); *C12Q 1/6869* (2013.01); *G01N 27/44713* (2013.01); *G01N 27/44791* (2013.01); *G01N 33/48721* (2013.01)

(58) Field of Classification Search
None
See application file for complete search history.

(56) References Cited

U.S. PATENT DOCUMENTS

2015/0108008 A1 4/2015 Kwok et al.
2015/0109008 A1 4/2015 Godin et al.

OTHER PUBLICATIONS

Rosenstein, Jacob K., et al.; Integrated nanopore sensing platform with sub-microsecond temporal resolution; vol. 9; No. 5; pp. 487-494; May 2012.
Kwok, Harold, et al.; Nanopore Fabrication by Controlled Dielectric Breakdown; vol. 9; Issue 3, pp. 1-6; Mar. 2014.
Notice of Allowance dated Mar. 20, 2020 in corresponding U.S. Appl. No. 15/104,325.
Non Final Office Action dated Nov. 19, 2018 in correpomding U.S. Appl. No. 15/104,325.
Non Final Office Action dated Oct. 24, 2019 in correponding U.S. Appl. No. 15/104,325.
Final Office Action dated May 15, 2019 in corresponding U.S. Appl. No. 15/104,325.

*Primary Examiner* — Nicholas A Smith
(74) *Attorney, Agent, or Firm* — Miles & Stockbridge, P.C.

(57) ABSTRACT

A pore forming method in which a pore is formed in such a way that a first voltage is applied between electrodes that are disposed with a film in an electrolytic solution therebetween; a second voltage, which is lower than the first voltage, is applied between the electrodes; a current that flows between the electrodes owing to the application of the second voltage is measured; it is judged whether a value of a current is equal to or larger than a predefined threshold; and if the value of the current is smaller than the threshold, the above sequence is repeated until a pore is formed. In this case, the second voltage is a voltage that makes the value ($I_{PF}$) of the current flowing through the film practically 0. With the use of the above method, a nanopore is formed in the film simply, easily, and accurately.

8 Claims, 14 Drawing Sheets

FIG. 2
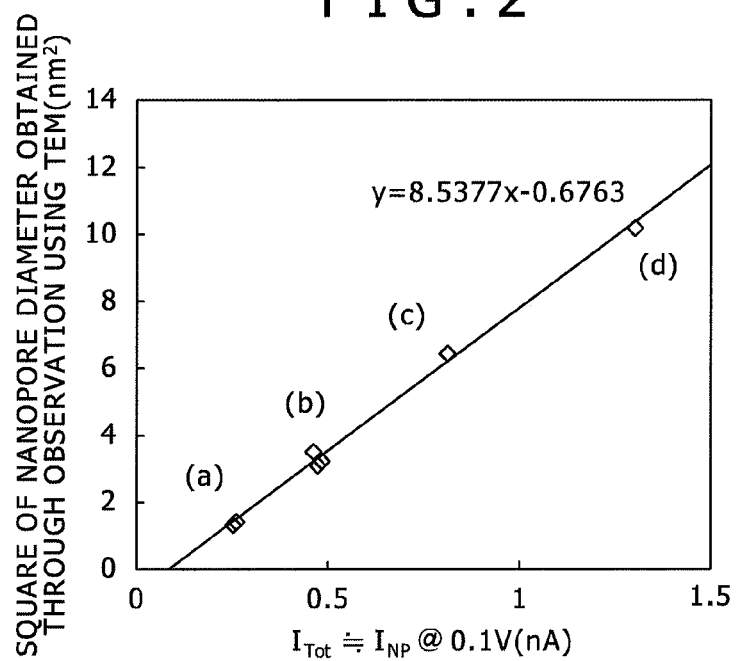
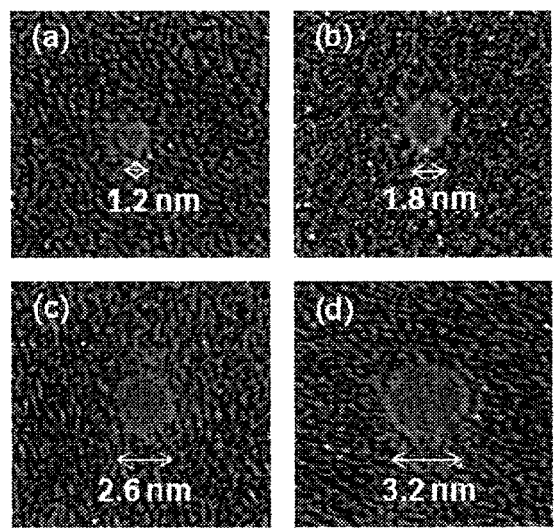

FIG.12
(A)
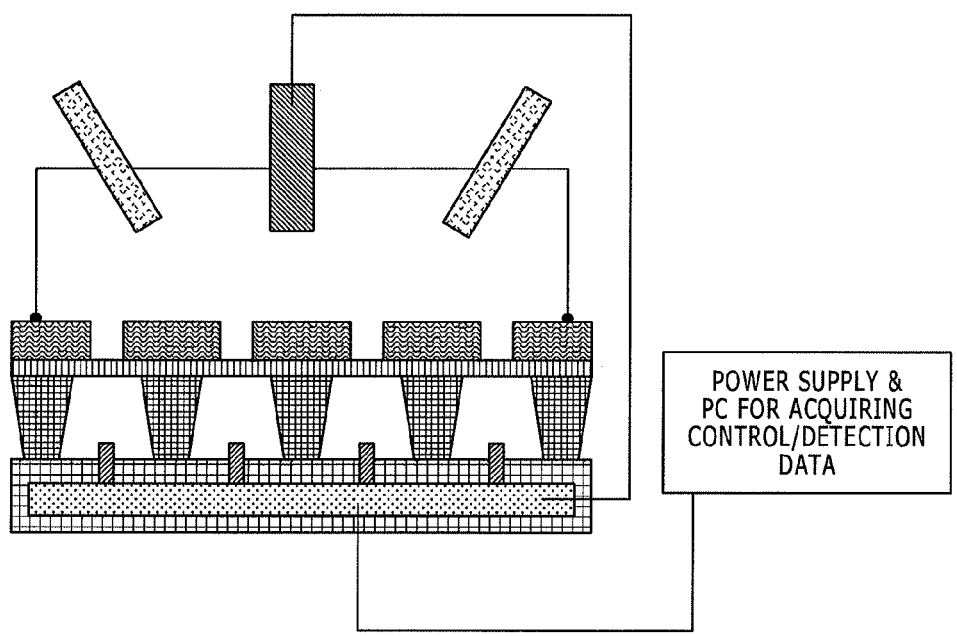
(B)
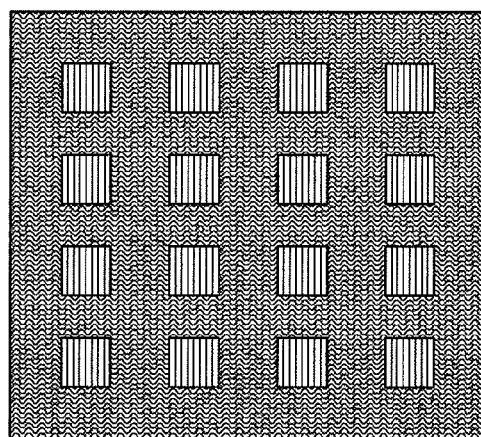

114  113

HOLE FORMING METHOD, MEASURING APPARATUS AND CHIP SET

TECHNICAL FIELD

The present invention relates to a technology about a sensor using semiconductors.

BACKGROUND ART

As one of approaches for realizing a third-generation DNA sequencer, a technology utilizing a nanopore has been widely investigated. In other words, this technology is a technology in which a pore whose size is almost equal to the size of a DNA (nanopore) is punctured through a thin film membrane; chambers located above and below the membrane are filled with aqueous solutions; an electrode is prepared in each chamber so that the electrode gets touch with the aqueous solution in each chamber; DNAs, which are measurement targets, are put in one of the chambers; and the time variation of an ion current flowing through two electrodes respectively prepared in both chambers is measured when DNAs are made to pass through the nanopore by electrophoretically accelerating the DNAs owing to the potential difference set between the electrodes, with the result that the structural characteristics and base sequences of the DNAs may be determined. In addition, the above method is useful for obtaining the structural characteristics of not only DNAs but also various biological molecules.

In the manufacture of nanopore devices, because of the high mechanical strength of nanopore devices and other reasons, manufacturing methods using semiconductor substrates, semiconductor materials, and semiconductor processes have drawn much attention. For example, a thin film membrane can be formed using a silicon nitride film (SiN film), and a nanopore whose diameter is equal to or smaller than 10 nm can be formed by reducing the irradiated area of an electron beam on the membrane and by controlling the energy and current of the electron beam with the use of a TEM (transmission electron microscope) apparatus (Nonpatent Literature 1).

In the process using the TEM apparatus, the size of a sample disposed in the apparatus is restricted, and furthermore it is usually difficult to simultaneously reduce the irradiated areas of electron beams for plural positions of a membrane. Therefore it is impossible to simultaneously process all chips on, for example, an 8-inch wafer, and it is necessary to cut off chips from the wafer and to process the chips one by one. Because a nanopore process is executed after the elapse of a long time owing to the vacuuming and stabilization of the TEM apparatus every time a chip is disposed in the apparatus, the throughput of the device formation decreases. In addition, because the drift of the electron beam radiation is virtually unavoidable, the variation of the diameter of a nanopore becomes a few nanometers. Furthermore, it is difficult to form nanopores whose diameters are equal to or smaller than 10 nm using patterning executed by a usual semiconductor lithography technique.

Nonpatent Literature 2 discloses a method for forming nanopores. The authors of Nonpatent Literature 2 disclose a method in which potassium chloride aqueous solutions (KCl aqueous solutions) are disposed above and below with a SiN film 10 nm thick that does not have pores therebetween, two electrodes are immersed in the KCl aqueous solutions of upper and lower chambers respectively, and a high voltage is applied between both electrodes. Furthermore, a certain cutoff current value is set in advance, and when a current between the two electrodes exceeds the cutoff current value, the application of the high voltage is stopped. As shown in FIG. 2(f) in Nonpatent Literature 2, if a voltage of 5 V is continuously applied, the current between the electrodes reaches the cutoff current value in 400 s to 500 s, and by stopping the application of the high voltage at this moment, a nanopore with its diameter about 5 nm is formed.

CITATION LIST

Nonpatent Literature

Nonpatent Literature 1: Jacob K Rosenstein, et al., Nature Methods, Vol. 9, No. 5, 487-492 (2012) Vol. 6, No. 4, 779-782 "Nonpatent Literature 2: Kwok, H.; Briggs, K.; and Tabard-Cossa, V., Nanopore Fabrication by Controlled Dielectric Breakdown"

SUMMARY OF INVENTION

Technical Problem

Problems that surface in the course of the experiment and examination of nanopore formation we executed using the method according to Nonpatent Literature 2 will be described in detail below.

When a high voltage is applied between an upper ion aqueous solution above a SiN membrane and a lower ion aqueous solution below the SiN membrane, for example, a positive voltage is applied to the upper ion aqueous solution and a negative voltage is applied to the lower ion aqueous solution, positive ions are accumulated on the upper side (surface side) of the SiN membrane and negative ions are accumulated on the lower side (back side) of the SiN membrane. It has become evident that, in the case where the applied voltage is high, charges having ions are conducted through the SiN membrane as a current that passes through the SiN membrane owing to the tunnel effect and a current that is conducted through the SiN membrane via defect levels in the SiN membrane (these two types of currents that pass through a membrane are referred to as a tunnel current and a Pool-Frenkel current respectively, and hereinafter in this specification, these currents that pass through a membrane (except for a current $I_{NP}$ that passes through a nanopore, and the currents $I_{NP}$ will be described later) will be generically referred to as a current $I_{PF}$). When charges are continuously conducted through the SiN membrane, the charges continue to break the bonds in the SiN membrane, and therefore the number of defect levels rapidly increases. The leakage current $I_{PF}$ that passes through the membrane increases accordingly. If the high voltage is continuously applied, the part of the SiN membrane that has the largest defect density is eventually penetrated and a nanopore is made, and then an ion current ($I_{NP}$) flows through the nanopore.

In other words, a current between the electrodes ($I_{tot.}$) can be given by the next expression.

$$I_{tot.} = I_{NP} + I_{PF}$$

Only $I_{PF}$ flows until the nanopore is opened. After the nanopore is opened, both $I_{NP}$ and $I_{PF}$ flow. If the ion density of an aqueous solution, the mobility of the ion, the thickness of a membrane, and the material quality of the membrane are grasped in advance, the size of an opened nanopore (the diameter of the nanopore) can be calculated from the amount of a current $I_{NP}$. In other words, after the high voltage is continuously applied, and when $I_{NP}$ corresponding to a desired pore diameter is formed, the application of the high voltage is stopped, with the result that a nanopore with the desired pore diameter can be formed.

However, it has become evident through our experiment that the values of $I_{PF}$ for individually fabricated membranes during the time when the high voltage is applied are different from each other because the numbers of defect levels and defect level densities of the membranes are different from each other even if the thicknesses of the membranes are the same. In addition, the value of $I_{PF}$ for a certain membrane during the time when the high voltage is applied varies with time owing to the increase in the number of the defects of the membrane, and ways in which the values of $I_{PF}$ for individual membranes vary with time are different from each other depending on the characteristics of the membranes. Furthermore, the above is true for the results described in Nonpatent Literature 2 (for example, for what are shown in FIG. 2(f) and FIG. S3). In the case where a pore with a certain diameter is fabricated, it is necessary to stop the application of a high voltage at the time when the value of $I_{NP}$ becomes a current value corresponding to a desired pore diameter. However, it is $I_{tot.}$ ($=I_{NP}+I_{PF}$) that can be measured actually between electrodes above and below a membrane, and therefore it is necessary to set a threshold current value (cutoff current value) as a value of $I_{tot.}$ for the sake of measurement. As described above, it has become evident that the value of $I_{PF}$ varies depending on individual membranes and with time even if the thicknesses of the membranes are the same, so that, even if a uniform cutoff current value is set for membranes with a certain membrane thickness to form pores therein, the sizes of the pores (diameters of the pores) vary.

In order to prevent the sizes of pores from varying, it is necessary to sequentially change a cutoff current value for each membrane and with time in accordance with the variation of $I_{PF}$. For this purpose, a unit is needed for sequentially memorizing cutoff current values that are different for individual membranes and vary with time and updating these cutoff current values, and therefore the amount of signal processing and the footprint of circuits for executing signal processing increase. The problem that the amount of signal processing and the footprint of circuits for executing signal processing increase becomes more serious in the case where an apparatus and a system for executing DNA measurement are built by integrating and parallelizing nanopore sensors. This is because the necessary number of nanopores is equal to the number of the parallelized nanopore sensors and one unit is needed for sequentially memorizing and updating a cutoff current value that varies with time for forming each of these nanopores. Therefore this becomes a barrier against downsizing the apparatus and the system and reducing the costs of the apparatus and the system.

In addition, there is another problem that it is necessary to form nanopores with their diameters nearly equal to the diameter of a single strand DNA (ssDNA) for a DNA sequence, so that pores with their diameters equal to 1 subnanometer to about 2 nm have to be formed accurately. In the case of using the parallelized nanopore sensors, the variations among the diameters of pores have to be controlled in the order of a few angstroms. If the variations among the diameters of the pores are large, signal processing specified for each sensor is needed, so that the calculation load of signal processing for the sensors becomes large because the detected current values of individual sensors at the time of DNA measurement have variations. Furthermore, in the case of analyzing data obtained by merging DNA measurement signals obtained from parallelized nanopore sensors, if there are large variations among detected current values obtained from the individual sensors, the existence of the large variations becomes one of factors that make the accuracy of the analysis decrease.

Looking at data disclosed in Nonpatent Literature 2 (refer to FIG. 2(f)), it is revealed that the current value changes by about 50 nA from the time when a high voltage (5 V) is applied to the time on which a mark "nanopore creation" is made. Here, in the case where a nanopore with its diameter 1.4 nm, which is suitable for DNA measurement, is formed in a SiN membrane with its thickness 10 nm (this membrane is used in Nonpatent Literature 2), $I_{NP}$ corresponding to the nanopore with its diameter 1.4 nm is about 10 nA when the voltage between the electrodes is 5 V. In other words, the fluctuation of the current value during the voltage application is larger than $I_{NP}$ corresponding to a desired pore diameter. In the forming process of nanopores, there is a case where a very small nanopore with its diameter 1 nm or smaller is generated in association with the application of voltage, and the nanopore gradually grows larger, and therefore it becomes difficult to judge whether $I_{NP}$ is gradually growing larger or $I_{PF}$ is increasing even if the current value $I_{tot.}$ is observed in such a slow forming process of nanopores. In other words, if the fluctuation of $I_{PF}$ with time is about equal to or larger than a desired $I_{NP}$, it becomes difficult to judge whether $I_{NP}$ is gradually growing larger or $I_{PF}$ is increasing. As a result, it is impossible to form a small nanopore with its diameter 3 nm or smaller by accurately controlling its diameter.

Solution to Problem

In order to solve the abovementioned problem, a method of forming a pore in a film according to the present invention includes: a first step of applying a first voltage between a first electrode and a second electrode, both first and second electrodes being disposed with the film in an electrolytic solution therebetween; a second step of applying a second voltage, which is lower than the first voltage, between the first electrode and the second electrode after the first voltage is applied and measuring a value of a current that flows between the first electrode and the second electrode owing to the application of the second voltage; and a third step of judging whether the value of the current is equal to or larger than a predefined threshold, wherein, if the value of the current is smaller than the threshold in the third step, the first step and the second step are repeated. In addition, the second voltage is a voltage that makes the value ($I_{PF}$) of a current flowing through the film practically 0.

Furthermore, an aspect of the present invention is a method of forming a pore that includes in the case where the value of the current exceeds the first threshold in the third step: a fourth step of applying a third voltage between the first electrode and the second electrode; a fifth step of applying the second voltage after applying the third voltage and measuring the value of a current that flows between the first electrode and the second electrode owing to the application of the second voltage; and a sixth step of judging whether the value of the current measured at the fifth step is a current value corresponding to a desired pore diameter with reference to data showing a relation between pore diameters and the values of currents, wherein the third voltage is a voltage that is lower than the first voltage, or a voltage that is equal to the first voltage and has a width of an application time smaller than a width of an application time during which the first voltage is most recently applied, and in the case where the value of the current is smaller than the current value corresponding to the desired pore diameter in the sixth step, the fourth step and the fifth step are repeated.

In addition, the following measurement apparatus is disclosed as another aspect according to the present invention. The measurement apparatus includes: a mechanism for installing a film in a chamber; a solution introducing opening for introducing an electrolytic solution into the chamber in which the film is installed; a first electrode and a second electrode installed with the film therebetween; a power supply for applying a voltage between the first electrode and the second electrode; a control circuit for controlling the voltage; a measurement unit for measuring a value of a current obtained by applying the voltage; and a memory unit for memorizing a relation between the size of a pore formed by applying the voltage to the film and the value of the current in association with the material and the thickness of the film. In this case, the value of the current is a current value measured at a voltage that makes the value of the current flowing through the film practically 0.

An aspect of the control circuit of the measurement apparatus applies a voltage, which makes a value of a current flowing through the film practically 0, between the first electrode and the second electrode after applying a first voltage between the first electrode and the second electrode; executes a first sequence for measuring a value of a current flowing between the first electrode and the second electrode using the measurement unit; judges whether the value of the current exceeds a predefined threshold or not; and repeats the first sequence if the value of the current is equal to or smaller than the threshold.

In addition, in the above aspect of the control circuit of the measurement apparatus, in the case where the value of the current exceeds the threshold, a voltage, which makes a value of a current flowing through the film practically 0, is applied between the first electrode and the second electrode after a third voltage is applied between the first electrode and the second electrode; a second sequence for measuring the value of a current flowing between the first electrode and the second electrode using the measurement unit is executed; and the third voltage is a voltage that is lower than the first voltage, or a voltage that is equal to the first voltage and has a width of an application time smaller than a width of an application time during which the first voltage is most recently applied, and in the case where the value of the measured current measured is smaller than a current value corresponding to a desired pore diameter, control for repeating the second sequence is executed.

Furthermore, in an aspect of the measurement apparatus, after a pore with the desired pore diameter is formed in the film, a specimen of nucleic acid to be introduced into the electrolytic solution is introduced into the pore by applying a voltage between the first electrode and the second electrode, and the value of a current induced by the specimen of nucleic acid passing through the pore is measured using the measurement unit.

In addition, as another aspect of the measurement apparatus, a chipset is disclosed in the present invention. The chipset includes: a film in which a pore is formed by applying a voltage; and a memory medium for memorizing a relation between the size of the pore formed by applying the voltage to the film and the value of a current in association with the material and the thickness of the film. In this case, the value of the current is measured at a voltage that makes the value ($I_{PF}$) of a current flowing through the film practically 0.

Advantageous Effects of Invention

Advantageous effects provided by typical embodiments inventions disclosed in this application will be described as follows. To put it briefly, according to this application, a nanopore can be formed in a membrane in a simpler and easier way and at a lower cost and more accurately as well than according to the related arts.

Problems, configurations, and advantageous effects other than those described above will be explicitly shown by explanations about the following embodiments.

BRIEF DESCRIPTION OF DRAWINGS

FIG. 2 An experimental result showing an advantageous effect of the present invention.

FIG. 12 A diagram showing an embodiment of the present invention.

DESCRIPTION OF EMBODIMENTS

Through all the drawings used for explaining the embodiments of the present invention, components having the same functions will be denoted by the same reference signs, and repeated explanations will be avoided as much as possible. Hereinafter, the embodiments of the present invention will be described in detail on the basis of the accompanying drawings. The configurations and materials of devices described in the embodiments are examples for materializing the spirit of the present invention, and they do not accurately specify the materials, dimensions, and the like of the devices.

First Embodiment

Figure 11:
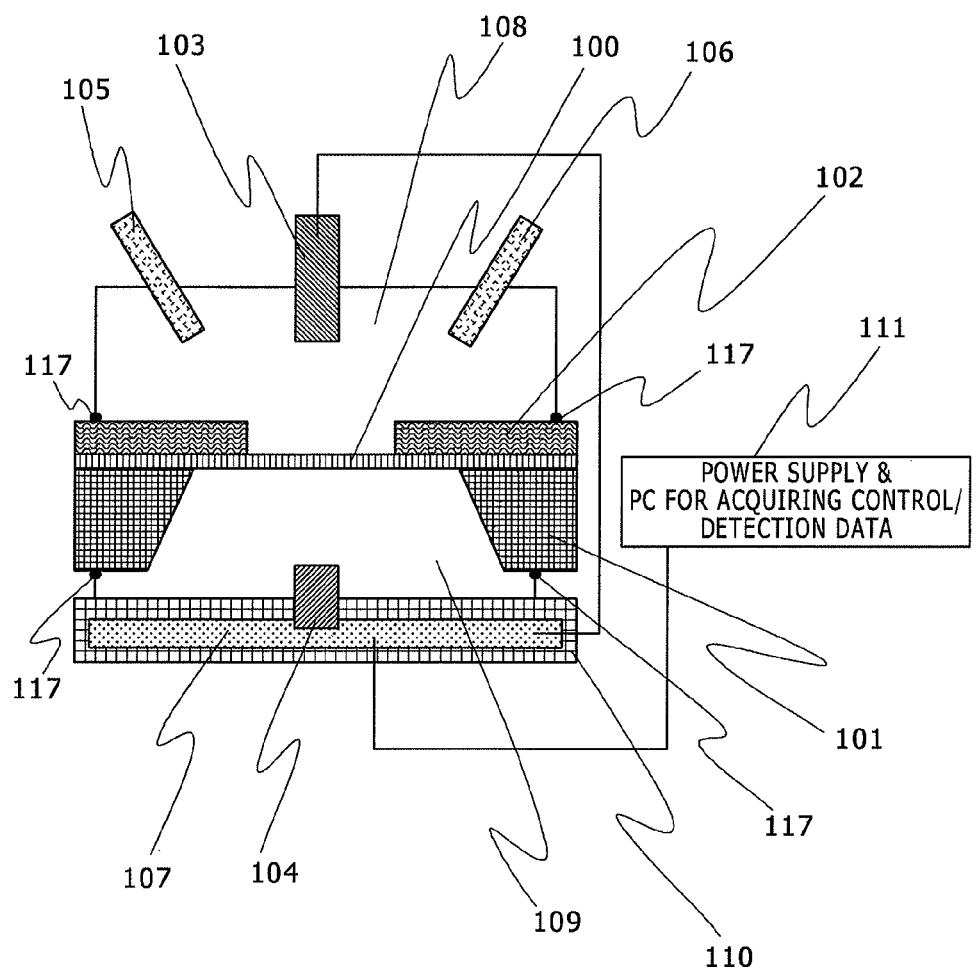
FIG. 11 A diagram showing an embodiment of the present invention.

First, an example of a nanopore forming apparatus and an example of a measurement system for measuring biological specimens such as a DNA is shown in FIG. 11. A reference sign 100 denotes a membrane such as a SiN film. A reference sign 101 denotes, for example, an Si substrate, and an around-membrane film 102 is, for example, an $SiO_2$ (silicon dioxide) film, an SiN film, or an $SiO_2$/SiN laminated film. A reference sign 103 denotes an upper electrode, and a reference sign 104 denotes a lower electrode, and the material of these electrodes is, for example, Ag/AgCl. Reference signs 105 and 106 denote filling/exhausting openings for filling and exhausting aqueous solutions and measurement targets (for example, DNAs). A reference sign 107 denotes a control circuit unit for executing a nanopore forming sequence. Reference signs 108 and 109 denote chambers filled with aqueous solutions and measurement targets. A reference sign 110 denotes a substrate for supporting the control circuit unit. A reference sign 111 denotes a power supply and a unit for executing the control of and aid for a total system such as the detection of measurement results, the input of the start of measurement, and the like. A reference sign 117 denotes an O-ring that is sandwiched between a chamber and a chip and used for preventing a solution in the chamber from leaking out to the outside as an example of a mechanism for setting a film. The control circuit unit 107 is not only in charge of executing the nanopore forming sequence, which will be described in this embodiment hereinafter, but also in charge of transferring signals during the measurement of a DNA to a PC and the like. Furthermore, it is preferable that the control circuit unit 107 should include an amplifier for amplifying detected currents, and an ADC. It goes without saying that there may be many cases such as a case where the amplifier is disposed in the control circuit unit 107 and the ADC is disposed outside the control circuit unit 107 (for example, in the unit 111), and it is important to build a system suitable for each measurement environment.

The abovementioned problem can be solved by using a method that will be descried in the following embodiment. Electrolytic solutions (aqueous solutions) are separated from each other with the membrane 100 therebetween, and electrodes are installed in the upper chamber 108 and the lower chamber 109 respectively so that these electrodes are immersed in the aqueous solutions. Next, a sequence in which, after applying a high voltage (Va) between these electrodes, a current between the electrodes $I_{tot.}$ is measured at a low voltage (Vb) (a voltage that makes $I_{PF} \cong 0 \ll I_{NP}$, that is, a voltage that makes $I_{PF}$ sufficiently smaller than $I_{NP}$ and almost 0) is repeated, and when $I_{tot.}$ exceeds a certain cutoff current value 1 (for example, 10 pA, that is, a current that passes through a nanopore with its diameter 1 nm or smaller), the sequence is stopped. The cutoff current value 1 can be determined in reference to a current value corresponding to a minimally necessary pore diameter and the like. Next, a sequence in which, after a voltage (Vc), which is lower than the voltage (Va) having been applied so far (but higher than the voltage (Vb)), is applied, $I_{tot.}$ is measured at the voltage (Vb), is repeated, and when $I_{tot.}$ reaches a cutoff current value 2 corresponding to a specified desired pore, the sequence is stopped.

According to the present method, because $I_{tot.}$ is measured at a low voltage that makes $I_{PF} \cong 0$, $I_{tot.}$ is nearly 0 until a nanopore is opened, and $I_{tot.}$ becomes nearly $I_{NP}$ at the time point when a very small pore is opened. Therefore, because the component of $I_{PF}$, which brings about the abovementioned problem and varies for each membrane and with time, can be made nearly 0 and can be neglected, even if the cutoff current value is uniformly specified, pores of the same size can be formed in membranes with thicknesses of the same size. In addition, according to the present method, it is not necessary to sequentially memorize and update a cutoff current value used for stopping the application of a high voltage for each membrane and with time, and the cutoff current value can be uniformly determined. Therefore, it becomes possible to reduce the amount of signal processing and the footprint of a circuit necessary for the signal processing, which leads to the downsizing and cost-reduction of the relevant apparatus. In particular, in the case where an apparatus and a system for executing DNA measurement are built by integrating and parallelizing nanopore sensors, although the necessary number of nanopores is equal to the number of the parallelized nanopore sensors, the cutoff current value can be uniformly specified for all the membranes, and a unit, which sequentially memorizes and updates a cutoff current value that varies with time for forming each nanopore, becomes unnecessary, which makes it possible to greatly reduce the size and the cost of the apparatus.

The reason why $I_{tot.}$ can be made nearly 0 or nearly $I_{NP}$ at the low voltage (Vb) can be verified on the basis of our experiments and examination results described below.

In other words, we have verified the following facts through a detailed analysis of a leakage current passing through a membrane in an aqueous solution with reference to some experiments. It has become evident that $I_{PF}$ in an aqueous solution is formed by the mixture of Pool-Frenkel currents that are conducted through hopping via defect levels in the membrane film and tunnel currents that are conducted through tunneling through the membrane film. Furthermore, an important thing that has been revealed as a result of our experiment is that $I_{PF}$ does not increase ohmically, but increases exponentially in response to the increment of an applied voltage. Therefore, it has become evident through our experiment that $I_{PF}$ becomes very large when the high voltage (Va), which is high enough to form a nanopore in a membrane, is applied, but $I_{PF}$ becomes very small when the low voltage (Vb), which is nearly 0 V, is applied. On the other hand, $I_{NP}$ ohmically increased in response to the increment of the applied voltage. Therefore, a situation where $I_{PF} \cong 0 \ll I_{NP}$ could be arranged at the low voltage (Vb) that was nearly 0 V, and in this case, a situation where the value of a current passing through electrodes was nearly equal to the value of a current passing through a nanopore was successfully realized. As a result, it became possible to detect the opening of a very small nanopore at the time point of the formation of the nanopore without the value of the current $I_{NP}$ being buried in the current value of $I_{PF}$ that increased or fluctuated with time during a high voltage was being applied.

Figure 1:
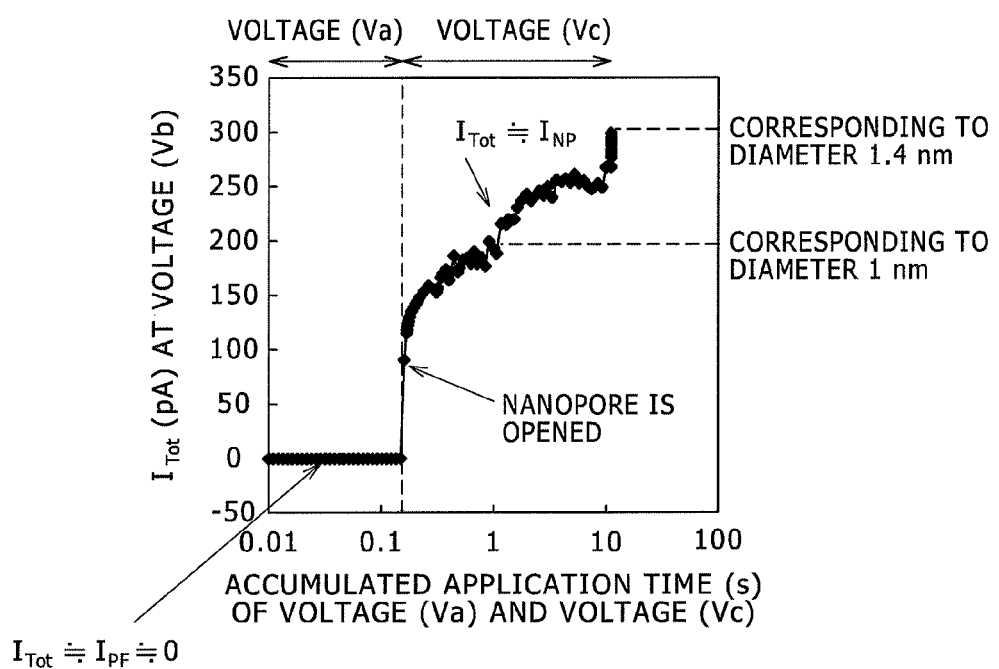
FIG. 1 An experimental result showing an advantageous effect of the present invention.

A result of the actual experiment is shown in FIG. 1. The horizontal axis of FIG. 1 represents the accumulated application time of the voltage (Va) or the voltage (Vc) that is lower than the voltage (Va), and the vertical axis of FIG. 1 represents the amount of the current $I_{tot.}$ that passes through the electrodes and is measured at the low voltage (Vb) (a voltage that makes $I_{PF} \cong 0 \ll I_{NP}$. A membrane used in this experiment is an SiN membrane, and its thickness is 10 nm. Chambers at the upper side and the lower side of the SiN membrane are filled with KCl aqueous solutions with their molarities 1 M, and electrodes 103 and 104 are immersed in the upper and the lower chambers respectively. The amount of current $I_{tot.}$ is a current passing between both electrodes. The voltage (Va), the voltage (Vb), and the voltage (Vc), which are used in this experiment, are 7 V, 0.1 V, and 3.5 V respectively. A sequence, in which the current $I_{tot.}$ between the electrodes was measured at the voltage (Vb) after the voltage (Va) was applied between the electrodes, was repeated, and when $I_{tot.}$ exceeded a certain cutoff current value 1 (10 pA which is corresponding to a current passing through a nanopore with its diameter 1 nm or smaller), the sequence was stopped.

Next, a sequence in which $I_{tot.}$ was measured at a voltage (Vb) after the voltage (Vc), which was lower than the voltage (Va) that had been applied so far, was applied, was repeated, and when $I_{tot.}$ reached 300 pA (corresponding to a pore diameter about 1.4 nm) that was a cutoff current value 2 corresponding to a desired pore diameter, the sequence was stopped. These current values, voltage values, a film thickness, and the like are only examples, and it goes without saying that values other than these values can be used. In addition, in the case where the voltage (Vc) is lower than the voltage (Va) or the voltage (Vc) is smaller than the voltage (Va), it means that the absolute value of the voltage (Vc) is smaller than the absolute value of the voltage (Va). Furthermore, the same can be said for the voltage (Vb).

It is known from the result of our experiment that the current $I_{tot.}$ between the electrodes is almost 0 before a nanopore is formed, and the value of the current 90 pA flows at the time point when the nanopore is opened. The nanopore, which is a small pore with its diameter smaller than 1 nm, is opened. Because $I_{tot.}$ ($\cong I_{PF}$) is nearly 0 just before the nanopore is opened, it is clearly understandable that the value of current $I_{tot.}$ is nearly equal to the value of the current $I_{NP}$ after the nanopore is opened. As a result, it becomes possible to detect the opening of a very small nanopore at the time point when the nanopore is formed without the value of the current passing through the electrodes being buried in the current value of $I_{PF}$ that increases or fluctuates with time while a high voltage is being applied. Furthermore, because the fluctuation of $I_{PF}$ is almost 0, even if the values of the cutoff currents 1 and 2 are set to uniform values respectively, pores of the same size can be formed. Unlike the related technologies, it is not necessary to sequentially memorize and update a cutoff current value used for stopping the application of a high voltage for each membrane and with time in this embodiment, and therefore the amount of signal processing and the footprint of a circuit for executing signal processing can be decreased, which makes it possible to reduce the size and the cost of the relevant apparatus.

In addition, the smaller the width of a single application time of the voltage (Va) is made, the smaller nanopore can be detected when the nanopore is opened. As described above, according to the present method, because $I_{tot.}$ ($\cong I_{PF}$) has been nearly 0 until just before a nanopore is opened, and the value of the current $I_{tot.}$ becomes nearly equal to the value of the current $I_{NP}$ after the nanopore is opened, it becomes possible to detect the opening of a very small nanopore at the time point when the very small nanopore is formed.

Next, a sequence in which, after the voltage (Vc) is applied after a small nanopore is once opened, $I_{tot.}$ is measured at the voltage (Vb), is repeated until $I_{tot.}$ becomes the cutoff current value 2 corresponding to a predefined and desired pore diameter, which makes it possible to form a nanopore with the desired diameter. Our examination has revealed that the mechanism in which a small nanopore, which has been once opened, becomes larger through the application of the voltage (Vc) is a mechanism in which atoms on the side wall of the nanopore are scraped away owing to the collisions and reactions of ions with the side wall, and the mechanism is different from a mechanism in which a pore is made in a membrane having no pores. Therefore, it is not necessary to use a high voltage such as the voltage (Va), and because the nanopore is gradually widened by applying the voltage (Vc) lower than the voltage (Va), the diameter of the nanopore can be more accurately controlled. In our experiment, in order to form a pore with its diameter 1.4 nm, the sequence was stopped at the time point when a current value corresponding to a diameter 1.4 nm was detected, but if this sequence is continued, it is of course possible to form a larger pore. (FIG. 1 shows an example in which pores with their diameter 1.4 nm or larger is formed using the present method. It is of course possible to form a nanopore with its diameter larger than diameters shown in FIG. 1.)

A relation between pore diameters and current values shown in FIG. 1 is calculated from a graph (FIG. 2) obtained in such a way that pores formed by the present method is observed using a TEM, the diameters of the pores are measured, and a relation between the values of $I_{tot.}$ ($\cong I_{NP}$) flowing between the electrodes measured at the voltage (Vb) and pore diameters is plotted. In FIG. 2, (a) denotes a diameter 1.2 nm, (b) denotes a diameter 1.8 nm, (c) denotes a diameter 2.6 nm, and (d) denotes a diameter 3.2 nm. As can be seen from the graph, a relation between the square of the nanopore diameter and the current value is clearly linear, and it is understandable from this result that the control of the nanopore diameter can be executed by managing the detected current value $I_{tot.}$ ($\cong I_{NP}$).

In other words, if, when a nanopore is made in a membrane made of a certain material and having a certain thickness, the size of the nanopore and a current value (current value measured at the voltage (Vb)) are checked out in advance, and a medium, which records a chip that has the membrane made of the same material and having the same thickness and a relation between the size of the nanopore and the current value when the nanopore is made in the membrane, is maintained, a desired pore can be formed using the above-described method. In the case where the measurement is executed at the voltage (Vb), because $I_{PF}$ is almost 0, and $I_{tot.}$ becomes $I_{NP}$, even if the numbers and densities of defect levels in various membranes are different from each other, a uniform cutoff current value can be used for managing desired pore diameters using the method according to the present invention.

By maintaining data that records membranes made of various materials and having various film thicknesses and a relation between the sizes of pores made in those membranes and current values, it becomes possible to form desired pores in the membranes made of various materials and having various film thicknesses. When it comes to the definition of the size of a nanopore when the nanopore is formed, it is an appropriate method to manage the size of the nanopore, for example, by regarding $2 \times$(the area of the nanopore viewed from up divided by the circular constant)$^{1/2}$ as the effective diameter of the nanopore.

According to the present method, as described above, because $I_{tot.} \cong I_{NP}$ is almost 0 until just before a nanopore is opened, and the value of the current $I_{tot.}$ becomes nearly equal to the value of the current $I_{NP}$ after the nanopore is opened, it becomes possible to detect the opening of a very small nanopore at the time point when the very small nanopore is formed. Therefore, as shown by the result of the present method, a very small nanopore with its diameter 1 nm or smaller can be formed, and additionally a nanopore with a desired diameter from a nanopore with its diameter 1 nm or smaller to a nanopore with its diameter 3 nm or larger can be formed with accuracy on the order of 0.1 nm or smaller. This means that, in the present method, a small pore diameter, which is smaller than the minimum diameter of a nanopore disclosed in Nonpatent Literature 2, can be formed in a controllable manner, which is one of advantageous points of the present method.

Figure 3:
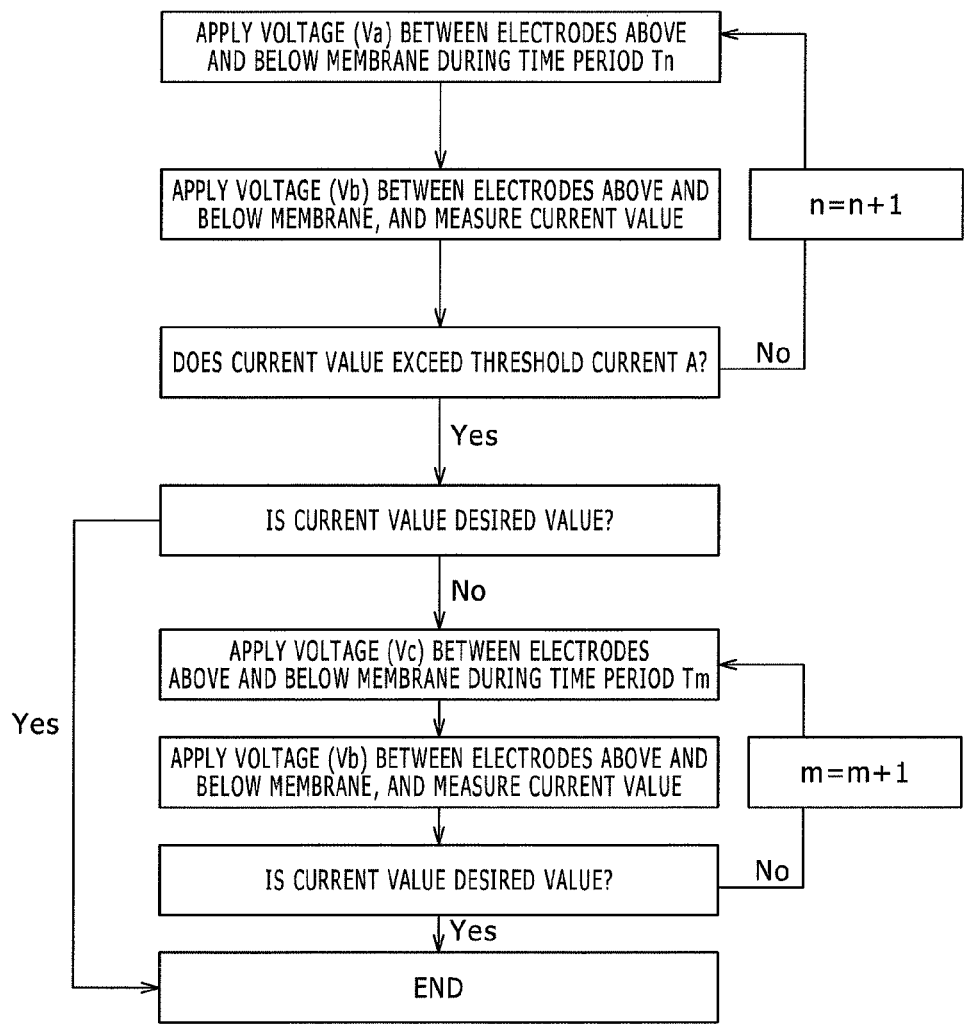
FIG. 3 A flowchart explaining an embodiment of the present invention.
Figure 4:
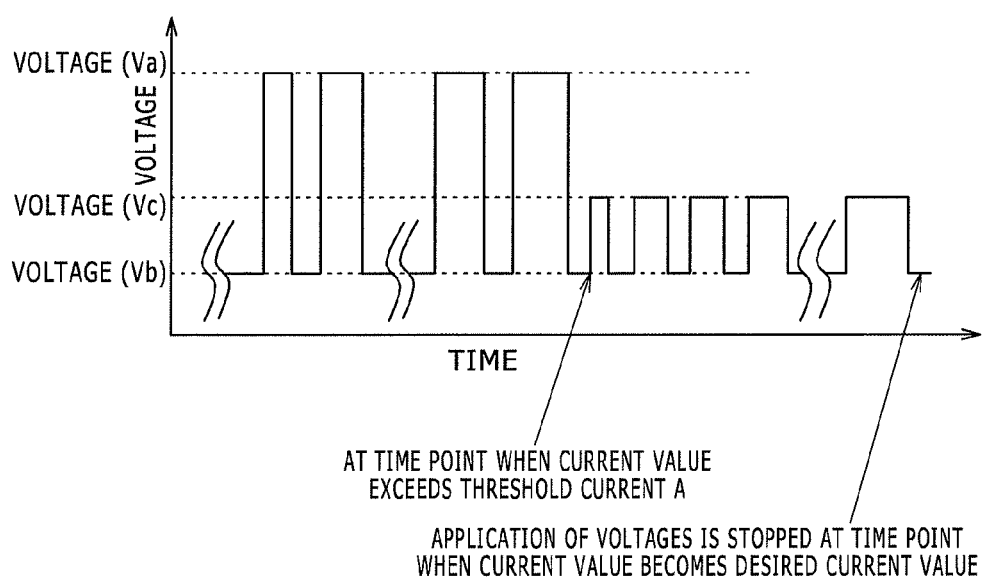
FIG. 4 A chart diagram explaining the embodiment of the present invention.

The sequence of a pore making method according to this embodiment is shown in FIG. 3. Furthermore, FIG. 4 shows an example of a pulse chart so that this embodiment is better understood. As for a threshold current A in FIG. 4, it is preferable that the threshold current A be set to a current corresponding a current value flowing through a pore with its diameter 1 nm or smaller.

In addition, the total width of application times of the voltage (Va) until a time point when a nanopore is formed varies from membrane to membrane even if the voltage (Va) of the same value is applied and the film thicknesses of membranes are the same because the membranes have the numbers and densities of defects different from each other. (Because there are various cases from a case where it takes 0.1 s at a voltage 0.7 V for a pore to be formed in a membrane to another case where it takes about 10 s at the voltage 0.7 V for a pore to be formed in another membrane, that is, the time widths of pore opening vary from membrane to membrane in different order of magnitude), if the width of an application time of a constant voltage (Va) is set in accordance with a membrane in which a pore is opened in a short time, it takes a very long time for a pore to be formed in a membrane in which a pore is opened in a long time. It takes a long time not because of the increase of the width of an application time of the voltage (Va), but because of the increase of the number of repetitions of the sequence of measuring a current at the voltage (Vb). Now let's represent the widths of an application time of the voltage (Va) by $T_{n+1}$, and $T_n$ ($T_{n+1} > T_n$), and it is effective to try to find how to shorten the width of an application time until a nanopore is opened. For example, in the case where the application time of the voltage (Va) is started with $T_1 = 10^{-2}$ s, the nth (n>1) application time of the voltage (Va) is set to $T_{n+1} = 10^{-2+0.1n} - 10^{-2+0.1(n-1)}$. In this case, even if the accumulated application time of the voltage (Va) required by nanopore opening varies in different order of magnitude, a time period from the start to the opening of a nanopore including a time required for the repetition of the sequence does not vary so much.

Furthermore, the voltage (Vb) is not a certain constant voltage, and currents are measured at plural points of voltages as long as the voltages make $I_{PF} \cong 0 \ll I_{NP}$ (for example, a voltage between 0.1 V and 0.4 V in our experiment). In this case, by confirming that the current-voltage characteristic of the measurement result is ohmic, the forming of a nanopore can be more certainly confirmed.

In addition, it is not always necessary that the voltage (vb) at which a current between the electrodes is observed until a nanopore is opened (voltage that makes $I_{PF} \cong 0 \ll I_{NP}$) is equal to the voltage (Vb) at which a current between the electrodes is observed in the process for widening the diameter of the nanopore (voltage that makes $I_{PF} \cong 0 \ll I_{NP}$), and the value of the voltage (Vb) can take any value as long as the value meets a relation of $I_{PF} \cong 0 \ll I_{NP}$. Furthermore, it is not always necessary that the polarity of the voltage (Vb) is equal to the polarity of the voltage (Va) or the polarity of the voltage (Vc), and it can be opposite to the polarity of the voltage (Va) or the polarity of the voltage (Vc) (as long as the voltage (Vb) meets the relation of $I_{PF} \cong 0 \ll I_{NP}$). In addition, it goes without saying that the shapes of the voltages (Va) and (Vc) do not have to be rectangular waves and, for example, sinusoidal waves that require time to rise can be applied between the electrodes as the voltages (Va) and (Vc).

It is desirable that the voltage (Va) be a voltage that generates an electric field 0.4 V/nm or larger in a membrane. Even if the electric field is smaller than 0.4 V/nm, there is a case where a pore is formed, but it takes a very long time for the pore to be opened, therefore it is desirable that the intensity of the electric field be 0.4 V/nm or larger in order to form the pore with a higher throughput. According to our examination, it became evident, in the case where an electric field that was applied to a membrane was set to 0.4 V/nm or larger, it took about an hour or shorter to form a nanopore in the membrane. It also became evident that, in the case where Va was set so that an electric field that was applied to the membrane became smaller than 0.4 V/nm, it took a long time that is, an hour or longer, to form a nanopore in the membrane. As for a DNA sequence or a measurement of other biological molecules using a nanopore, it is expected to take an hour or shorter to carry out the measurement itself if the measurement is comparably short although the required time is dependent on the kind of the measurement. Therefore, if it takes an hour or longer to form a nanopore in a membrane, a time from the formation of the nanopore to the end of the measurement expands to several times the measurement time, which leads to the large reduction of the total throughput. In order to prevent the total throughput from being largely reduced, it is desirable that a time period until the formation of a nanopore in the membrane be an hour or shorter, and therefore it is preferable that the voltage (Va) be set so that the electric field applied to the membrane is 0.4 V/nm or larger.

In addition, it is preferable that the voltage (Vb), which makes $I_{PF} \cong 0 \ll I_{NP}$, be set lower so that an electric field applied to the membrane is 0.3 V/nm or smaller. Even if the electric field applied to the membrane is larger than 0.3 V/nm at the time when the voltage (Vb) is applied, if the voltage (Vb) is lower than the voltage (Va), the advantageous effect brought about by this embodiment can be obtained somewhat. However, according to our examination, in order that it may bring $I_{PF}$ closer to almost 0, and the pore formation and the diameter of the pore may be precisely controlled, it is preferable that the electric field applied to a membrane be 0.3 V/nm or smaller and the voltage (Vb) be set lower.

According to our examination, in the case where $I_{PF}$ is measured at the voltage (Vb) that makes the electric field applied to a membrane 0.3 V/nm or smaller, $I_{PF}$ becomes very much smaller than a current that flows through a pore having its diameter equivalent to 0.1 nm. The size of a nanopore that is a target of the present invention is a size through which mainly a DNA and a biological molecule can pass, and a nanopore whose diameter is at least 0.1 nm is a target of the present invention. Therefore, the voltage (Vb) that makes an electric field applied to a membrane 0.3 V/nm or smaller can be said to be the voltage (Vb) that makes $I_{PF} \cong 0 \ll I_{NP}$. Therefore, with the use of the voltage (Vb) that makes an electric field applied to a membrane 0.3 V/nm or smaller, the formation of a nanopore with its diameter 0.1 nm or larger can be accurately detected. Furthermore, because $I_{PF}$ becomes very much smaller than a current that flows through a pore having its diameter equivalent to 0.1 nm, and $I_{PF}$ becomes very much smaller than $I_{NP}$, it is possible to grasp the size of a formed pore with a degree of accuracy on the order of 0.1 nm or smaller with reference to the value of $I_{Tot.}$ ($\cong I_{NP}$).

The abovementioned relations can be put differently in terms of voltages, and it is desirable that the voltage (Va) and the Voltage (Vb) be set to meet the following inequalities.

Voltage $(Va) \geq 0.4$ V/nm×thickness of membrane (nm),

Voltage $(Vb) \leq 0.3$ V/nm×thickness of membrane (nm).

It is preferable that the voltage (Vb) be set so that $I_{PF} \leq \frac{1}{5} \times$(threshold current value A), and it is more preferable that the voltage (Vb) be set so that $I_{PF} \leq \frac{1}{10} \times$(threshold current value A), and owing to the above settings, easier signal detection can be made. In other words, there are some cases where, if the threshold current value A is not higher than current noises that are generated by peripheral electromagnetic waves or vibrations and that interfere with $I_{Tot.}$ ($\cong I_{PF}$) at the time of measurement, it is erroneously judged that a nanopore has been formed although the nanopore has not been formed, and a sequence for forming the nanopore is stopped. The current noises that are generated by peripheral electromagnetic waves or vibrations and that interfere with $I_{Tot.}$ ($\cong I_{PF}$) at the time of measurement are about one tenth to one fifth of $I_{Tot.}$ ($\cong I_{PF}$). Therefore, by preferably setting the voltage (Vb) so that $I_{PF} \leq \frac{1}{5} \times$(threshold current value A), and by more preferably setting the voltage (Vb) so that $I_{PF} \leq \frac{1}{10} \times$(threshold current value A), it becomes possible to surely detect the opening of a nanopore at the time when the nanopore is formed without fail.

In addition, it is desirable that the voltage (Va) be set to 1.0 V/nm or smaller. If the voltage (Va) is set larger than 1.0 V/nm, there is so much stress on a film when the voltage (Va) is applied that the size of a pore becomes very large when the pore is measured at the voltage (Vb) after the pore is formed in a membrane. To explain it in detail, in the case of the voltage (Va)>1.0 V/nm, it is impossible to detect the opening of a pore with its diameter 1 nm or smaller at the time when the pore is formed unlike the experiment example of the present invention unless the width of a single voltage application time is set very small. However, according to our examination, even if the width of a single voltage application time was made as short as possible within the capability of the current semiconductor/circuit technology, it was difficult to detect the opening of a pore with its diameter 1 nm or smaller at the time when the pore was formed in the case of the voltage (Va)>1.0 V/nm. Therefore, it is desirable that the voltage (Va) be set to 1.0 V/nm or smaller. With such a setting, pores with their diameters 1 nm or smaller can be formed accurately and with a good yield ratio.

In addition, it is also desirable that the voltage (Vb) be 10 mV or higher. If the voltage (Vb) is 10 mV or lower, the value of $I_{NP}$ becomes small, and it becomes difficult to detect the forming of a small pore at the time when the pore is formed.

A good way to decide the width of a voltage (Va) application time is to decide how many times a sequence, in which a current value is measured at the voltage (Vb) after the application of the voltage (Va), is repeated while the measuring time increases one digit. As described above, the application time of the voltage (Va), which is applied until a nanopore is formed, varies in different order of magnitude even if the voltage (Va) of the same value and a membrane with the same film thickness are used. (In our experiment, there are many cases from a case where a nanopore is formed in 0.1 s at the voltage 7 V to a case where a nanopore is formed in about 10 s at the voltage 7 V.) According to our examination, it is known that a nanopore with its diameter 1 nm or smaller can be formed by adopting a sequence in which a current is measured at the voltage (Vb) after the voltage (Va) is applied four times or more while the measuring time increases one digit, and it is also known that the larger the number of repetitions of the sequence becomes, the larger the probability that a nanopore with its diameter 1 nm or smaller is formed becomes. In particular, according to our experiment, it is known that a nanopore with its diameter 1 nm or smaller can be formed with a 100% by adopting a sequence in which a current is measured at the voltage (Vb) after the voltage (Va) is applied 24 times or more while the measuring time increases one digit.

According to the present method, as shown by an aftermentioned embodiment for example, a membrane substrate is disposed between chambers just before a DNA measurement, a pore is formed by the above-described method after aqueous solutions are injected into the chambers, and without removing the membrane substrate from the chambers after the pore is formed, measurement can be executed after DNAs are injected into one of the chambers. Therefore, because, after the nanopore is formed, the nanopore is not exposed to contaminated materials in the atmosphere, a lot of noises are not measured. Furthermore, the manufacturing cost by the present method is greatly reduced and throughput of nanopores formed by the present method is greatly improved in comparison with those of nanopores formed using a TEM apparatus. In addition, the control of the sizes of nanopores is greatly improved in comparison with that of nanopores formed using t a TEM apparatus. Furthermore, in the case where it is desired that plural measurements be executed using integrated/parallelized nanopore sensors, if membranes with no pores are integrated and parallelized and electrodes are disposed so that voltages can be applied to the individual membranes, pores can be formed in the membranes in parallel in aqueous solutions before the DNA measurements, and then the DNA measurements can be executed in parallel without delay.

Second Embodiment

An embodiment in which the formation and control of a pore executed in the sequence of the first embodiment are more accurately executed is shown in this embodiment. As shown in a sequence of FIG. 5, it becomes possible to discharge charges, which are accumulated in a membrane by applying the voltage (Va), by applying a voltage (Vd) whose polarity is opposite to that of the voltage (Va) during a time period between the application of the voltage (Va) and the measurement of $I_{tot.}$ at the voltage (Vb). Owing to this discharge, a current component generated by discharging currents charged in the membrane can be reduced at the time of current measurement at the voltage (Vb), which makes it possible to reduce noise currents included in $I_{tot.}$. With the above reduction of the noise currents, it becomes possible to measure $I_{NP}$ more accurately at the time of nanopore formation, and therefore it becomes possible to manage the formation and sizes of pores more accurately.

Figure 5:
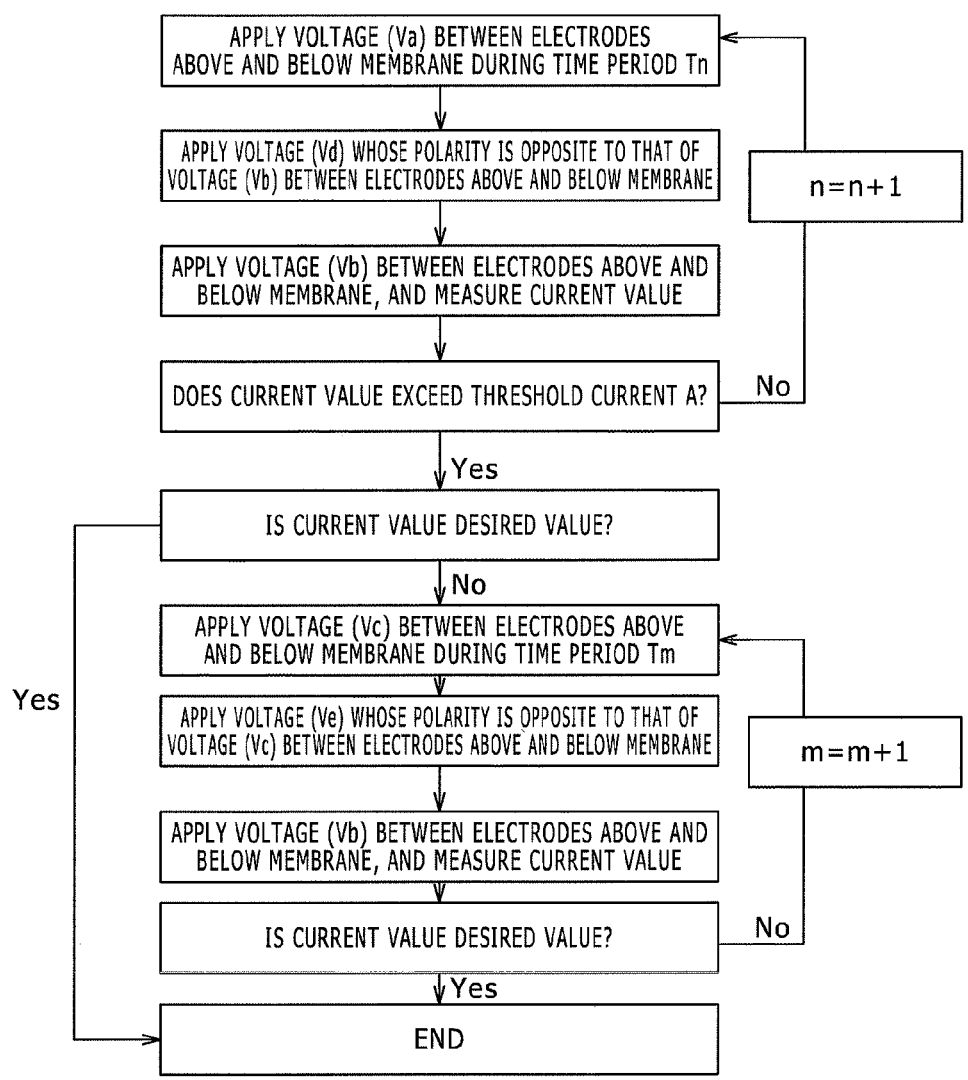
FIG. 5 A flowchart explaining an embodiment of the present invention.

In addition, as shown in FIG. 5, in a sequence in which, after a nanopore is formed, the nanopore is widened (a sequence in which the voltage (Vc) is applied, and a current is measured at the voltage (Vb)), the application of a voltage (Ve), whose polarity is opposite to that of the voltage (Vc) in a time period after the voltage (Vc) is applied and before a current is measured at the voltage (Vb), is effective in removing foreign substances (pieces of dirt) that may clog up the nanopore. In other words, in the case where the foreign substances (pieces of dirt), which are charged, are pulled by the nanopore when the voltage (Vc) is applied, and the foreign substances (pieces of dirt) clog up the nanopore, the foreign substances (pieces of dirt) are removed from the nanopore by applying a voltage whose polarity is opposite to that of the voltage (Vc), with the result that the nanopore is prevented from being clogged by the foreign substances (pieces of dirt).

It goes without saying that the shapes of the voltages (Vd) and (Ve) do not have to be rectangular waves and, for example, sinusoidal waves that require time to rise can be applied between the electrodes as the voltages (Vd) and (Ve).

Figure 6:
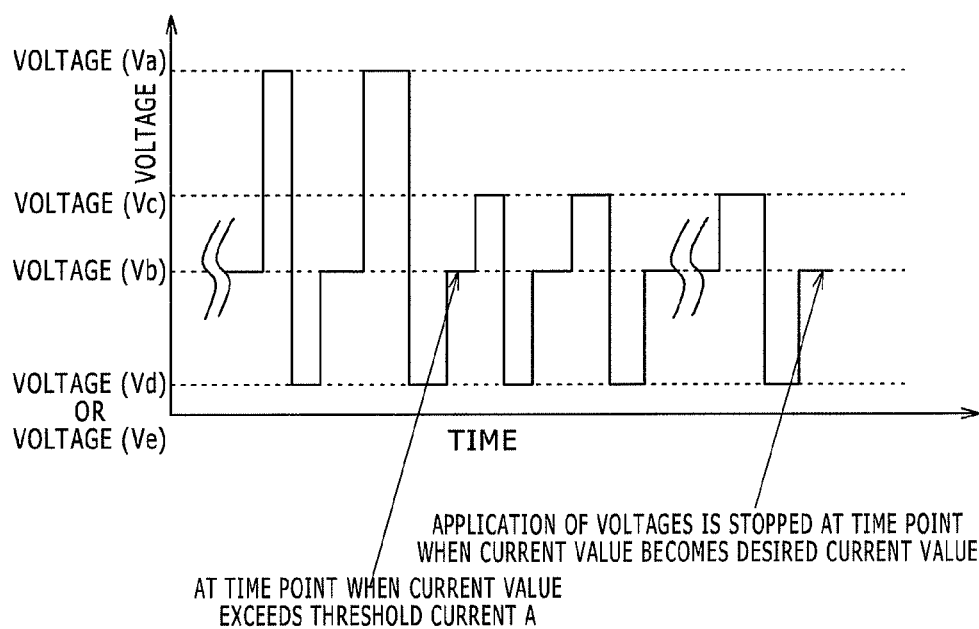
FIG. 6 A chart diagram explaining the embodiment of the present invention.

Furthermore, FIG. 6 shows an example of a pulse chart so that this embodiment is better understood.

Third Embodiment

After a nanopore is opened, in a process in which the nanopore is widened (in a sequence in which the voltage (Vc) is applied, and a current is measured at the voltage (Vb)), the sequence can be executed by setting the value of the voltage (Vc) the same as that of the high voltage (Va). In this case, however, the width of a single voltage (Vc) application time (denoted by Tm in FIG. 3 to FIG. 7) has to be very narrow. In particular, the width of a voltage (Vc) application time at the time when the voltage (Vc) is first applied has to be narrower than that of a voltage (Va) application time at the time when the voltage (Va) is most recently applied. This is because, if a nanopore, which has been once opened, is processed at a voltage equal to the high voltage (Va) and with the wide width of a single voltage application time without modification, the speed with which the pore is widened is too large for the widening of the diameter of the pore to be controlled. In other words, in order to control the diameter of a pore, the magnitude of the voltage (Vc) has to be smaller than that of the voltage (Va), or, if both magnitudes are the same, the width of a voltage (Vc) application time has to be narrower than that of a voltage (Va) application time. According to the present method, because the magnitude of the voltage (Va) can be set the same as that of the voltage (Vc), the number of types of voltages can be reduced by one, and therefore the load on the relevant control circuit can be reduced. As a result, the footprint of the relevant circuits and the cost of the relevant system can be reduced.

Fourth Embodiment

Figure 7:
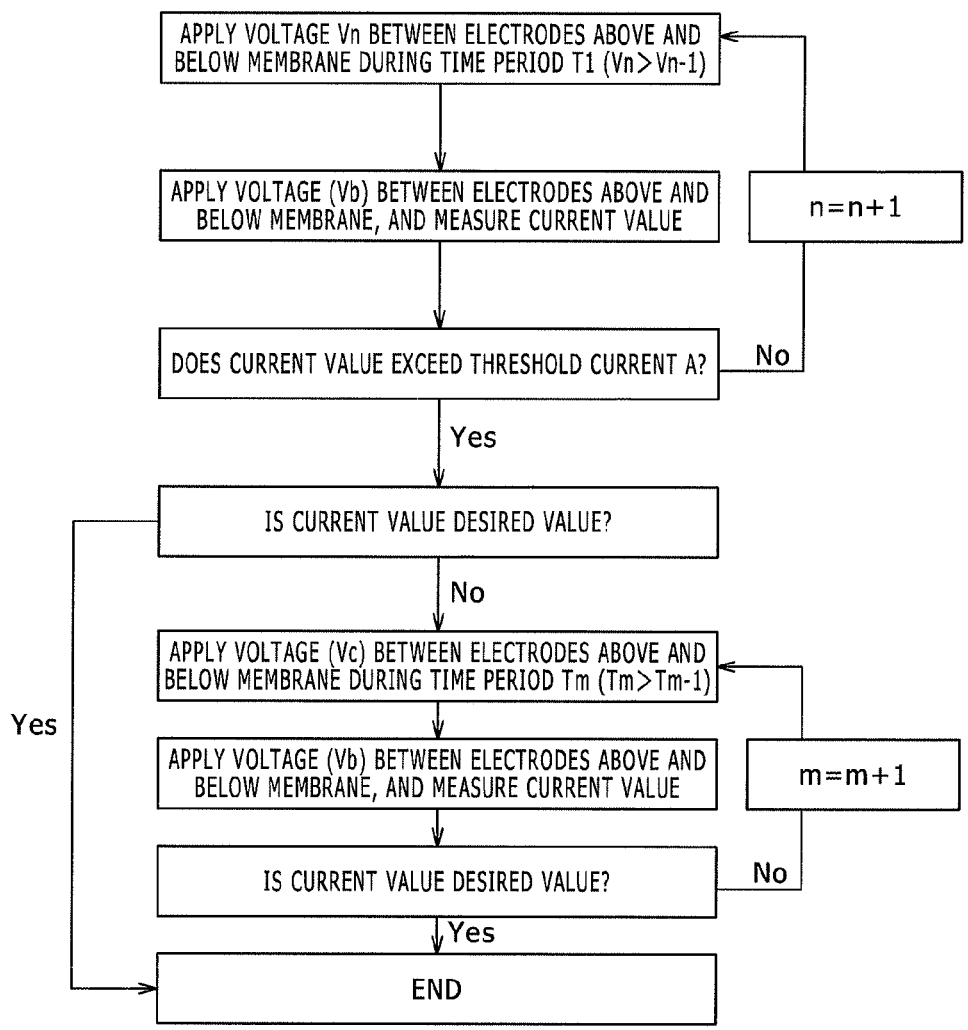
FIG. 7 A flowchart explaining an embodiment of the present invention.

Another method that has almost the same advantageous effects as the first embodiment has will be shown in this embodiment. As shown in FIG. 7, the magnitude of a voltage, which is corresponding to the voltage (Va) that has been used so far in the first embodiment to third embodiment, is set variable. Next, after applying a rather low voltage $V_1$ first during a time $T_1$, a current that flows between electrodes above and below a membrane is measured at the voltage (Vb) (a voltage that makes $I_{PF} \cong 0 \ll I_{NP}$) that is lower than the voltage $V_1$, and it is checked whether a nanopore is opened or not (that is, whether the current is larger than a threshold current A or not). If the current is not larger than the threshold current, a sequence, in which a voltage $V_2$ higher than the voltage $V_1$ is applied during the time $T_1$, a current that flows between electrodes above and below the membrane is measured at the voltage (Vb) (a voltage that makes $I_{PF} \cong 0 \ll I_{NP}$) that is lower than the voltage $V_1$, and it is checked whether a nanopore is opened or not (that is, whether the current is larger than the threshold current A or not), is repeated until the current becomes larger than the threshold current A in order to open a nanopore.

Figure 8:
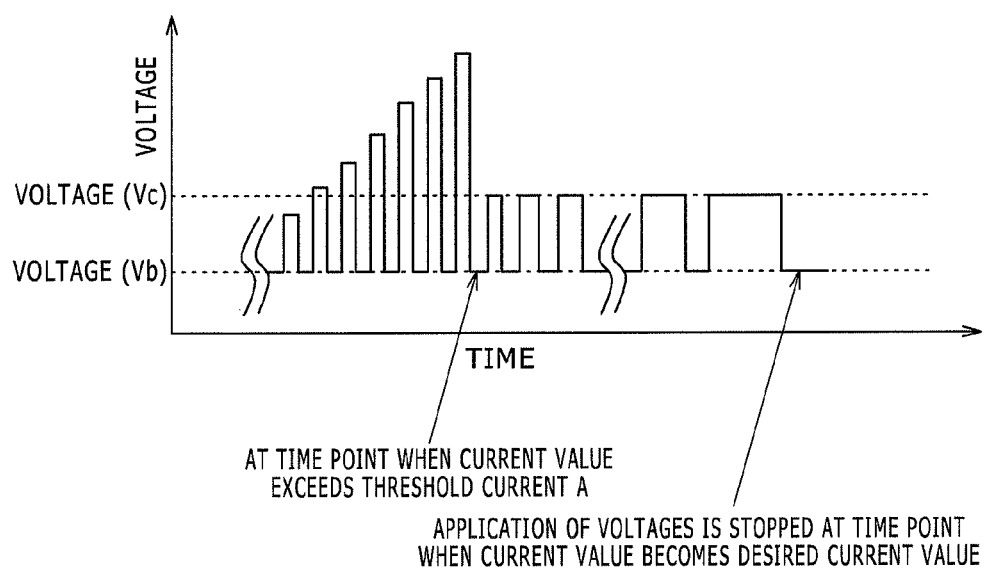
FIG. 8 A chart diagram explaining the embodiment of the present invention.

FIG. 8 shows an example of a pulse chart so that this embodiment is better understood. In other words, the application time of the voltage $V_n$ that is applied for the nth time is set the same and it is not dependent on the number of n, and the magnitude of the voltage $V_n$ is increased along with the repeat number of n. As the value of $V_{n+1}-V_n$ is set smaller, the formation of the smaller nanopore can be detected at the time when the smaller nanopore is formed. It can also be true in the present method that $I_{tot.}$ ($\cong I_{PF}$) is almost 0 just before the nanopore is opened, and because, after the nanopore is opened, $I_{tot.} \cong I_{NP}$, an advantageous effect equivalent to that provided by the first embodiment is also brought about by the present method.

Figure 9:
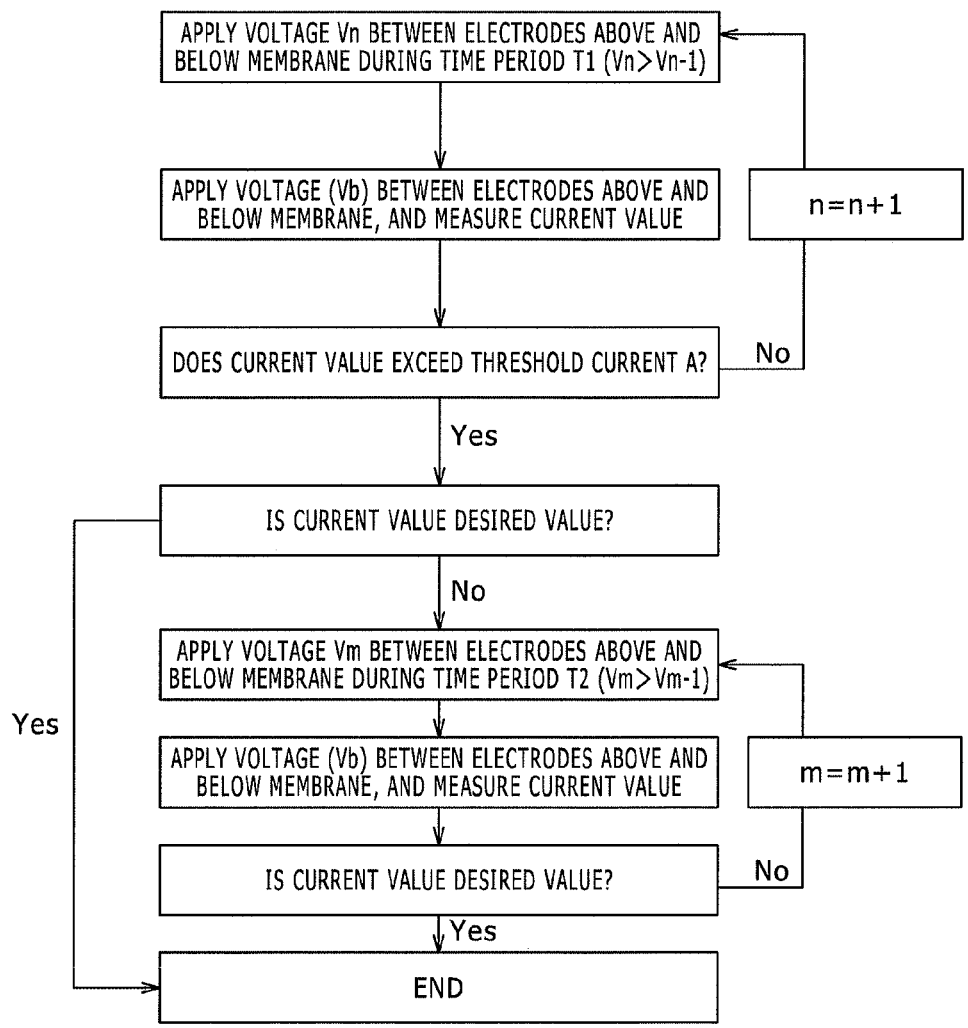
FIG. 9 A flowchart explaining an embodiment of the present invention.
Figure 10:
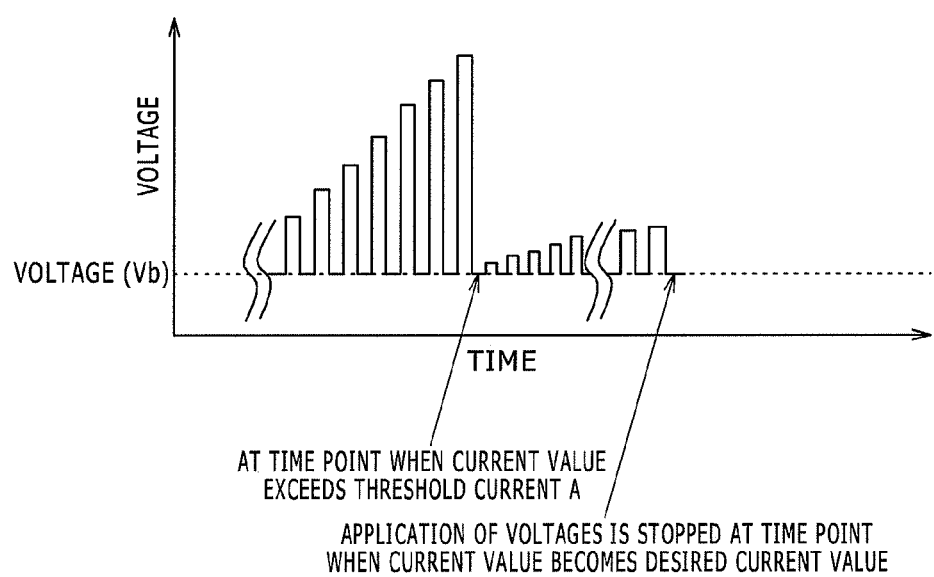
FIG. 10 A chart diagram explaining the embodiment of the present invention.

As shown in FIG. 9, the present method is also applicable to the sequence in which, after a nanopore is formed, the nanopore is widened. FIG. 10 shows an example of a pulse chart so that the above sequence is better understood. In other words, a voltage $V_m$ that is applied for the mth time in order to widen the nanopore is set so that $V_{m+1}$ is higher than $V_m$, and the application time $T_2$ of the voltage $V_n$ is set fixed regardless of m. The smaller the value of $V_{n+1}-V_m$ is, the more gradually the diameter of the nanopore can be widened, and therefore the diameter can be more accurately controlled.

In addition, an effect similar to that obtained in the second embodiment is also brought about by adding a procedure, in which a voltage with its polarity reversed is applied, to the sequence of this embodiment.

In addition, it goes without saying that the shapes of the voltages $V_n$ and $V_m$ do not have to be rectangular waves and, for example, sinusoidal waves that require time to rise can be applied between the electrodes as the voltages $V_n$ and $V_m$.

The present method is useful in the case where the value of the voltage (Va) needed for a pore to be formed in a constant time largely differs depending on individual membranes.

Fifth Embodiment

The nanopore forming method that uses any of techniques described in the first embodiment to the fifth embodiment is useful for forming nanopores in inorganic material membranes (such as an SiON membrane, $SiO_2$ membrane, an $Al_2O_3$ membrane, an $HfO_2$ membrane, An HfSiON membrane, a $TiO_2$ membrane, a $ZrSiO_4$ membrane, a $Y_2O_3$ membrane), a graphene membrane, other polymer films as well as an SiN membrane.

Sixth Embodiment

An example of a procedure in which an actual DNA measurement is executed will be shown below with reference to FIG. 11. First, a chip including a membrane 100 (the chip includes, for example, the membrane 100, an Si substrate 101, and an around-membrane film 102) is set in chambers, and an upper part above the membrane and a lower part below the membrane are filled with KCL aqueous solutions. Furthermore an electrode 103 is installed above the membrane, and an electrode 104 and a control circuit unit 107, both of which are supported by a substrate 110, are installed below the membrane. The control circuit unit 107 is configured to be able to control the electrodes 103 and 104. A mechanism for installing the chip includes O-rings that seals gaps between the chip and the chambers in order to prevent the solutions in the chambers from leaking outside.

After the abovementioned settings are finished, the nanopore formation using one of the sequences shown in the first embodiment to fourth embodiment is executed first. For example, the voltage of the electrode 103 is set to 0 V, voltage applications and current measurements at low voltages are repeated using the voltages shown in the previously-mentioned embodiments (the voltage (Va), the voltage (Vb), the voltage (Vc), the voltage (Vd), the voltage (Ve), the voltage Vn, the voltage Vm) as voltages of the electrode 104, and the above sequence is controlled by the control circuit unit 107 so that a nanopore with a desired diameter is formed.

After the nanopore is formed, the solution that has been used up to now is replaced with a solution including measurement targets (DNAs) via the filling opening 105 and the exhausting opening 106 so that the upper chamber 108 is filled with the solution including the measurement targets (DNAs). Afterward, if the voltage of the electrode 103 is set to 0 V, and the voltage of the electrode 104 is set to a voltage suitable for DNA measurement (for example, 0.5 V) using the control circuit unit 107, the measurement targets DNAs in the upper chamber are electrophoretically drawn to the nanopore, and when the DNAs pass through the nanopore, the variation of an ion current flowing between the electrodes 103 and 104 is detected by the control circuit unit. This signal is transmitted through the control circuit unit 107 or through an amplifier or an ADC located outside the control circuit unit 107 to a PC, and the structural characteristics and base sequences of the DNAs can be determined through the data analysis executed by the PC. For example, because the values of currents that flow when A, T, C, and G, which constitute a DNA, pass through a pore are different from each other, the sequence of the DNA can be measured from variations in the currents.

Alternatively, it is conceivable that, at the time when a desired nanopore is formed, the chip is brought out from the chambers and stored and the measurement is executed at a later date (that is, the chip for the measurement is fabricated in advance). In addition, there can be another way in which, DNAs of measurement targets are put in the solution in the upper chamber 108 to save time before forming a nanopore, and after the nanopore is formed through the nanopore forming sequence, DNA measurement is started without replacing the solution.

Furthermore, as shown in FIG. 2, when a nanopore is formed in a membrane that is made of a certain material and has a certain film thickness, if the size of the nanopore and the value of a current at that time (the value of a current measured at the voltage (Vb)) are checked in advance, a desired pore can be formed using techniques shown by the above-described embodiments by maintaining a chip that has a membrane that is made of the same material and has the same film thickness, and a medium, which records a relation between the size of the nanopore and the value of the current, as a set. If there is a data sheet that records membranes made of various materials and having various film thicknesses and a relation between the sizes of pores formed in these membranes and the values of currents, or if there is the relevant apparatus in which apart recording the above data is embedded, desired pores can be formed in the membranes made of various materials and having various film thicknesses.

Seventh Embodiment

FIG. 12(A) shows an example of a nanopore forming apparatus and an example of a DNA measurement system corresponding to DNA measurement using paralleled nanopore sensors. FIG. 12(A) shows that the portion of the installed film that gets into touch with the solution is divided into a plurality of parts, each of which is under a membrane and filled with an aqueous solution, and each of the parts are isolated from each other with substrates 101. Each substrate 101 is made of an insulating material, or the surface of each substrate 101 is covered with an insulating material. FIG. 12(B) is the top view of membranes or the plurality of parts of the film formed in parallel on the substrate.

Figure 13:
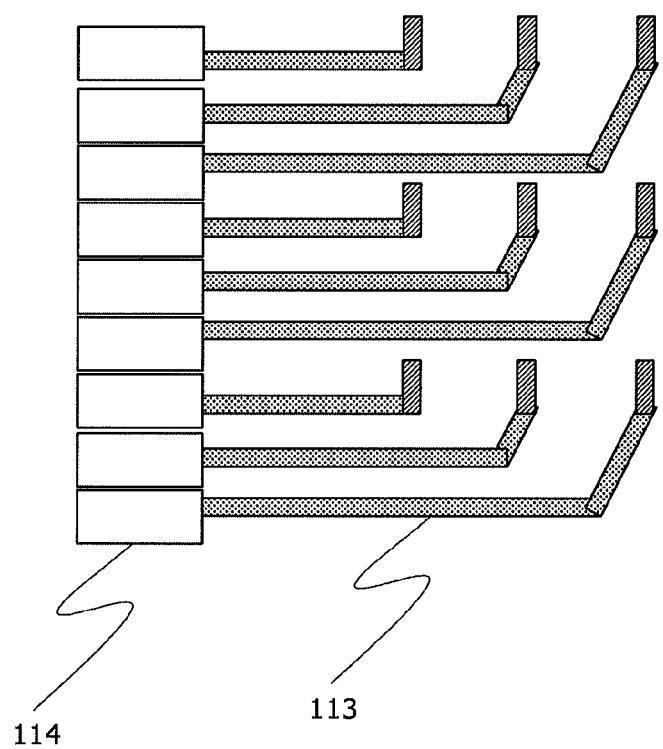
FIG. 13 A diagram showing an embodiment of the present invention.

A nanopore forming sequence and a DNA measurement sequence executed on each membrane are the same as described in the sixth embodiment. An upper electrode above the membrane is given a fixed voltage, the voltages of lower electrodes below the membrane are respectively controlled, and a current at each of the lower electrodes is observed. The internal structure of the control circuit unit 107 is, for example, shown in FIG. 13, and a unit 114, which is in charge of a voltage input into each lower electrode 104 and the measurement of a current detected at each lower electrode 104, is installed for each membranes. Each unit 114 includes a control mechanism (which is in charge of a sequence of nanopore formation according to a technique shown by any of the above-described embodiments, and additionally, plays a role in transmitting signals of the DNA measurement to a PC, and includes an amplifier for amplifying currents and an ADC) as shown in the sixth embodiment. Each of the units 114 is connected to the relevant lower electrode 104 with a hard-wiring 113.

Figure 14:
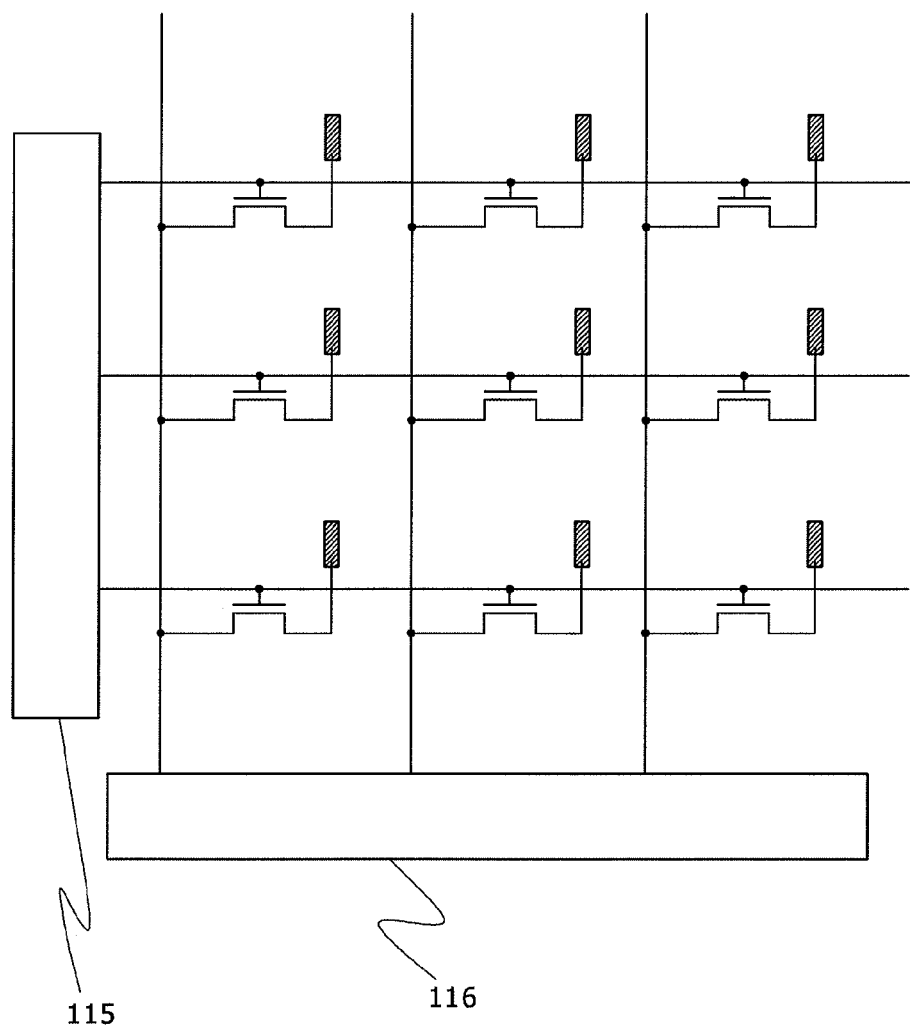
FIG. 14 A diagram showing an embodiment of the present invention.

In addition, as shown in FIG. 14, it is conceivable that, in order for electrical connections to the respective lower electrodes 104 to be controlled in an array fashion, selection transistors (switches) are provided for the lower electrodes 104 respectively. 115 is configured to be able to control the voltages of selection transistors in each row, and 116 is configured to be able to detect currents flowing from the respective lower electrodes 104 and to be able to apply voltages to the respective lower electrodes at the time of nanopore formation or DNA measurement as well. The operation method of this embodiment is performed in such a way that, if it is requested that the voltage (Va) is applied to a membrane at an intersection point between a first row and a first column, the voltage of the upper electrode is set to 0 V, and a voltage that turns on selection transistors is applied to a wiring on the first row, and a voltage that turns off selection transistors is applied to wirings on other rows. At the same time, the voltage (Va) is applied to a wiring on the first column, and a voltage that is the same as that of the upper electrodes is applied to wirings on other columns. In such a way, the voltage (Va) is applied only between the upper electrode and the lower electrode at the intersection point between the first row and the first column.

Furthermore, if it is requested that the voltage (Va) is applied between the upper electrode and all the lower electrodes on the first row, the voltage of the upper electrode is set to 0 V, and a voltage that turns on selection transistors is applied to a wiring on the first row, and a voltage that turns off selection transistors is applied to wirings on other rows. At the same time, the voltage (Va) is applied to wirings on all columns. Afterward, if, for example, a nanopore is formed in a membrane at the intersection point between the first row and the first column, the application of the voltage (Va) to the first column is stopped, and the application of the voltage (Va) to other columns, in membranes on which nanopores have not been formed, and the readout of currents at the low voltage (Vb) are repeated. By repeating such a sequence, nanopores can be formed in membranes on the first row. After nanopores are formed in all the membranes on the first row, the similar sequence is repeated on membranes on a second row, on a third row and so on until nanopores are formed in all the membranes.

In addition, even at the time of measurement of measurement targets such as DNAs, the measurement can be executed by repeating current measurement on nanopores on each row at a high speed in such a way.

By configuring the control circuit unit 107 in such a way (as shown in FIG. 14), it becomes possible to reduce the footprint of the circuit in comparison with a case where a voltage application/current measurement unit 114 is provided for each membrane (because parts of the voltage application/current measurement unit can be shared), which leads to the cost reduction of the relevant apparatus/system.

Furthermore, as shown in FIG. 2, when a nanopore is formed in a membrane that is made of a certain material and has a certain film thickness, if the size of the nanopore and the value of a current at that time (the value of a current measured at the voltage (Vb)) are checked in advance, a desired pore can be formed using techniques shown by the above-described embodiments by maintaining a medium that records a chip, which has a membrane that is made of the same material and has the same film thickness, and a relation between the size of the nanopore and the value of the current. If there is a data sheet that records membranes made of various materials and having various film thicknesses and a relation between the sizes of pores formed in these membranes and the values of currents, or if there is the relevant apparatus in which a part recording the above data is embedded, desired pores can be formed in the membranes made of various materials and having various film thicknesses.

LIST OF REFERENCE SIGNS

100: MEMBRANE
101: SUBSTRATE
102: AROUND-MEMBRANE FILM
103: UPPER ELECTRODE
104: LOWER ELECTRODE
105: FILLING/EXHAUSTING OPENING
106: FILLING/EXHAUSTING OPENING
107: CONTROL CIRCUIT UNIT
108: CHAMBER ABOVE MEMBRANE
109: CHAMBER BELOW MEMBRANE
110: SUPPORTING SUBSTRATE
111: POWER SUPPLY AND CONTROL/DETECTION DATA ACQUISITION UNIT (PC)
113: HARD-WIRING
114: VOLTAGE APPLICATION/CURRENT MEASUREMENT CONTROL UNIT
115: SELECTION TRANSISTOR CONTROL UNIT
116: VOLTAGE APPLICATION/CURRENT MEASUREMENT CONTROL UNIT
117: MECHANISM FOR SETTING FILM

The invention claimed is:

1. A measurement apparatus comprising:
a chamber having a solution introducing opening constructed for introducing an electrolytic solution into the chamber;
a first electrode and a second electrode installed with a film therebetween;
a power supply for applying a voltage between the first electrode and the second electrode;
a control circuit for controlling the voltage; and
a measurement unit for measuring a value of a current obtained by applying the voltage,
wherein the control circuit is programmed to apply a second voltage, which makes a value of a current flowing through the film contained in the chamber, before a hole is opened in the film, to be less than 90 pA, between the first electrode and the second electrode, after applying a first voltage between the first electrode and the second electrode; execute a first sequence for measuring a value of a current flowing between the first electrode and the second electrode using the measurement unit; determine whether the value of the current exceeds a predefined threshold or not; and repeat the first sequence if the value of the current is equal to or smaller than the threshold.

2. The measurement apparatus according to claim 1, wherein, in the case where the value of the current exceeds the threshold, the second voltage, which makes the value of the current flowing through the film before the hole is opened to be less than 90 pA, is applied between the first electrode and the second electrode after a third voltage is applied between the first electrode and the second electrode; a second sequence for measuring the value of the current flowing between the first electrode and the second electrode using the measurement unit is executed; the third voltage is a voltage that is lower than the first voltage, or is a voltage that is equal to the first voltage and has a width of an application time smaller than a width of an application time during which the first voltage is most recently applied; and in the case where the value of the measured current measured is smaller than a current value corresponding to a desired pore diameter, control for repeating the second sequence is executed.

3. The measurement apparatus according to claim 2, wherein, after a pore with the desired pore diameter is formed, a specimen of nucleic acid to be introduced into the electrolytic solution is introduced into the pore by applying a measurement voltage between the first electrode and the second electrode, and a value of a current induced by the specimen of nucleic acid passing through the pore is measured using the measurement unit.

4. The measurement apparatus according to claim 1, wherein a portion of the installed film that gets into touch with the solution is divided into a plurality of parts by insulating materials, the second electrode is installed for each of the plurality of parts divided by the insulating materials, and the control circuit is programmed to control the first and second voltages applied to each of the plurality of parts individually.

5. The measurement device according to claim 4, wherein the control circuit is programmed to apply a potential difference between the first electrode and the second electrode for a first portion of the plurality of parts of the installed film, so that one of the first and second voltages is applied to the first portion of the plurality of parts of the installed film, and while said one voltage is applied to each of the first portion of the plurality of parts, the first electrode and the second electrode for a second portion of the plurality of parts other than the first portion of the plurality of parts of the installed film are at the same potential.

6. The measurement apparatus according to claim 5, further comprising a selection transistor provided corresponding to the respective second electrode for controlling the application of the first and second voltages to the first portion of the plurality of parts of the installed film and the non-application of the first and second voltages to the second portion of the plurality of parts of the installed film.

7. The measurement apparatus according to claim 1, further comprising a memory unit for memorizing a relation between the size of a pore formed by applying the first and second voltages to the installed film and the value of the current in association with the material and the thickness of the installed film.

8. The measurement apparatus according to claim 7, wherein the memory unit stores a relationship between a size of the pore formed by applying the first and second voltages to the installed film and a current value based on the material and the thickness of the installed film.

\* \* \* \* \*